United States Patent [19]
Ikemura et al.

[11] Patent Number: 5,264,513
[45] Date of Patent: Nov. 23, 1993

[54] PRIMER COMPOSITION

[75] Inventors: Kunio Ikemura, Joyo; Yoshiaki Kouro, Hirakata, both of Japan

[73] Assignee: Kabushiki Kaisha Shofu, Kyoto, Japan

[21] Appl. No.: 863,780

[22] Filed: Apr. 6, 1992

[30] Foreign Application Priority Data

Feb. 15, 1990 [JP] Japan .................. 2-34777

[51] Int. Cl.$^5$ .............. A61K 6/083; C08F 20/10; C08F 22/10
[52] U.S. Cl. .................. 526/318; 523/116; 523/118; 526/318.5
[58] Field of Search ......... 523/116, 118; 524/556; 526/318, 318.5

[56] References Cited

U.S. PATENT DOCUMENTS

| | | | |
|---|---|---|---|
| 4,148,988 | 4/1979 | Masuhara et al. | 526/318 |
| 4,521,550 | 6/1985 | Bowen | 523/116 |
| 4,538,990 | 9/1985 | Pashley | 433/217 |
| 4,553,941 | 11/1985 | Aasen | 433/228.1 |
| 4,593,054 | 6/1986 | Asmussen et al. | 523/118 |
| 4,719,149 | 1/1988 | Aasen et al. | 523/116 |
| 4,880,660 | 11/1989 | Aasen et al. | 523/116 |
| 5,089,051 | 2/1992 | Eppinger et al. | 523/116 |

OTHER PUBLICATIONS

Journal of Dental Research, vol. 34(6), pp. 849-853, (1955), "A Simple Method of Increasing the Adhesion of Acrylic Filling Materials to Enamel Surfaces", Buonocore.

IADR/AADR Abstracts No. 915 p. 276 (1985), "Effects of Ferric Oxalate Purity on Adhesive Bonding to Dentin", Bowen et al.

Journal of Dental Research, vol. 63(8), pp. 1087-1089 (1984), "Bond Strength Between Dentin and Restorative Resins Mediated by Mixtures of HEMA and Glutaraldehyde", Munksgaard et al.

Scand. J. Dent. Res. vol. 93, pp. 463-466 (1985), "Dentinpolymer bond mediated by glutaraldehyde/HEMA", Munksgaard et al.

International Dental Journal, vol. 35, pp. 160-165 (1985) "Bonding of restorative resins to dentine promoted by aqueous mixtures of aldehydes and active monomers", Asmussen et al.

Proceedings of the 1st International Congress on Dental Materials, pp. 236-237 (1989).

Primary Examiner—Paul R. Michl
Assistant Examiner—Peter Szekely
Attorney, Agent, or Firm—Stevens, Davis, Miller & Mosher

[57] ABSTRACT

The present invention provides a primer composition comprising (i) 0.5-90% by weight of water, (ii) 5-90% by weight of a polymerizable compound having hydroxyl group, (iii) 0.1-90% by weight of a polymerizable compound having acidic group, and (iv) 0.01-30% by weight of a curing agent. When dental adhesive restorative materials such as dental resin cements, composite resins, PMMA resins and the like are made to adhere directly or through bonding agents to substrates such as vital hard tissues, especially an enamel or a dentin of natural teeth, glass ionomer cements and the like, the primer composition is able to impart a strong and durable adhesive property between the both without treating said substrates with an acid and the like.

21 Claims, No Drawings 5,264,513

PRIMER COMPOSITION

BACKGROUND OF THE INVENTION

1. Field of the Invention

The present invention relates to a primer composition. More particularly, the present invention relates to a primer composition which, when dental adhesive restorative materials such as dental resin cements, composite resins, polymethylmethacrylate (PMMA) resins and the like are made to adhere directly or through bonding agents to substrates such as vital hard tissues, especially an enamel or a dentin of natural teeth, glass ionomer cements and the like, is able to impart a strong and durable adhesive property between both without treating said substrates with an acid and the like.

2. Description of the Prior Art

Dental restorative resins are in general insufficient in their adhesive property to teeth such that restorative materials may fall off or that there may occur secondary caries, pulpal irritation, marginal fracture or marginal discoloration due to invasion or leakage of bacteria at the margin of restoration, causing problems in dental clinic.

To solve these clinical problems, techniques to improve the adhesive property between the restorative materials and teeth have been proposed in the prior art, as described in detail below.

A proposal of the so-called acid etching technique is now being evaluated clinically as a technique for adhesion to the enamel [Journal of Dental Research, Vol. 34(6), pp. 849-853, (1955)]. Adhesion by this technique is based not on the chemical bonding between the teeth and adhesive resins but on mechanical anchor effect caused by curing and anchoring of the resins that have penetrated into a honeycomb structure mainly formed by demineralization of enamel prisms. However, this honeycomb structure is not formed on the surface of the enamel which is not subjected to the acid etching treatment and adhesive property in this case remains still insufficient.

Recently much interest has been focused on adhesion to the dentin and many proposals have been made increasingly, with the result of some improvements. These proposals are, however, concerned with the method wherein the dentin is pretreated, or reformed and reinforced in some cases, by using inorganic acids, organic acids, organic acids and some kinds of metal chlorides, or ethylenediaminetetraacetic acid (EDTA) or their salts. Apart from the case of the enamel, clinical problems are pointed out in these methods when they are applied to the dentin. Etching treatment of the dentin especially by using phosphoric acid has caused many discussions in Japan as well as in Europe and United States, and American Dental Association expressed a recommendation against the phosphoric acid treatment of the dentin. However, citric acid and oxalic acid are yet taken into account for the acid treatment agent of the dentin since they are considered to have less etching effect than phosphoric acid [see IADR/AADR Abstracts No. 915, p. 276 (1985) or U.S. Pat. No. 4,521,550 and No. 4,538,990]. Treatment methods using EDTA are also proposed [see U.S. Pat. No. 4,553,941 and No. 4,593,054]. However, dental society or dentists desire so strongly a method yielding a strong and durable adhesive strength of the dentin without subjecting it to any acid treatment.

Meanwhile, adhesive strength to the dentin have remarkably progressed in recent years. It is reported that an adhesive strength of 100 kgf/cm$^2$ or more was reached by using a conventional bonding material and a composite resin, wherein the dentin was treated with a mixed solution of glutaraldehyde, water and 2-hydroxyethyl methacrylate (named as Gluma) after a pretreatment with a solution of EDTA.Na salt [Journal of Dental Research, Vol. 63(8), pp. 1087-1089 (1984); Scand. J. Dent. Res., Vol. 93, pp. 463-466 (1985); and International Dental Journal, Vol. 35, pp. 160-165 (1985)]. It is proved, however, that when the dentin is not subjected to the EDTA.Na treatment, a value of about 30.9 kgf/cm$^2$ is actually shown, indicating that the value still remains low.

In Proceedings of the 7th Meeting of Japan Society for Adhesive Dentistry, pp. 121-122 and pp. 123-124 (1989), or in Proceedings of the 1st International Congress on Dental Materials, pp. 236-237 (1989) and The Journal of Dental Engineering No. 90, pp. 31-38 (1989), it is reported that high adhesive strength is maintained by methylmethacrylate (MMA)/partially oxidized tri-nu-butylborane (TBB-O) resin even after 2000 times of thermal cycles by using cool water (4° C.) and hot water (55° C.), wherein the dentin has been subjected to, a primer treatment using a mixed solution of solution A [70% of 2-hydroxyethylmethacrylate (2-HEMA)+6% of o-methacryloxytyrosinamide (MTYA)] and solution B (2% of glutaraldehyde), which is so-called above-described Gluma type of treatment solution, after an acid treatment of the dentin. For example, it is reported that an adhesive strength of 164 kgf/cm$^2$ is obtained by a mixed primer treatment of the above-described solution A and solution B after a treatment with 40% of phosphoric acid. On the other hand, an adhesive strength of 48 kgf/cm$^2$ to the dentin without acid treatment is shown even at 0th cycle, which is indicative that not only the power is insufficient in a sense of the intrinsic adhesive strength but also durable adhesive property to the dentin without acid treatment is hardly obtained. Although adhesive strength is improved by this method, it is still low against the dentin without acid treatment in a strict sense. The proposer of the above-described technique has recognized in the disclosures that the intrinsic adhesive strength to the dentin has not been reached yet.

More recently, a primer composition which does not require any pre-treatment such as acid treatment, i.e. a primer composition for hard tissues comprising water, a water soluble film-forming agent and salts of acids, has been proposed (see Japanese Patent KOKAI No. 113057/1989).

When the primer composition is used for making a composite resin adhere to the dentin of teeth, however, the adhesive strength is largely influenced by the kinds and blending amounts of acid salts, thereby causing difficulties that not only the resulting adhesive strength may be inferior to that obtained by using no primer composition, but also durable adhesive property is not obtained.

SUMMARY OF THE INVENTION

The present invention has been achieved to provide a primer composition which can solve the above-described problems and which, when dental adhesive restorative materials such as dental resin cements, composite resins, PMMA resins and the like are made to adhere directly or through bonding agents to substrates such as vital hard tissues, especially an enamel or a dentin of natural teeth, glass ionomer cements and the like, is able to impart a strong and durable adhesive property between the both without treating said substrates with an acid and the like.

The inventors of the present invention found that, through concentrated studies on primers to impart the durable adhesive property, a primer composition comprising (i) 0.5-90% by weight of water preferably 10-55% by weight of water, (ii) 5-90% by weight of a compound having hydroxy groups, and polymerizable unsaturated groups and preferably 20-60% by weight of a compound having hydroxy groups and polymerizable unsaturated groups, (iii) 0.1-90% by weight of a compound having acidic groups, and polymerizable unsaturated groups, preferably 2.5-60% by weight of a compound having acidic groups and polymerized unsaturated groups, and (iv) 0.01-30% by weight of a curing agent, preferably 0.03 to 10% by weight of the curing group is able to solve the above problems in the prior art and that, when dental adhesive restorative materials such as dental resin cements, composite resins, PMMA resins and the like are made to adhere directly or through bonding agents to substrates such as vital hard tissues, especially an enamel or a dentin of natural teeth, glass ionomer cements and the like, the primer composition is able to give a strong and durable adhesive property between the both without treating said substrates with an acid and the like. The present invention was completed based on the findings described above.

DETAILED DESCRIPTION OF THE INVENTION

Water which is stable on storage and acceptable as an ingredient for medical use, and does not intrinsically contain any harmful impurities to the components and adhesive effect of the composition is preferably used in this invention. Distilled water (or purified water) or ion-exchange water (or deionized water) is suitable. The blending amounts of water are in general in the range of 0.5-90% by weight, preferably 5-80% by weight and more preferably 10-50% by weight. The amount of less than 0.5% by weight causes a deterioration in adhesive property while the amounts of more than 90% by weight also causes a decrease in adhesive property.

The compounds having hydroxy group and polymerizable unsaturated group which are used in this invention are polimerizable monomers, oligomers or polymers having polymerizable unsaturated group such as acryloyl group, methacryloyl group, vinyl group, acrylic group and the like together with hydroxy group, the monomers being particularly preferable.

Examples of these kinds of compounds are; 2-hydroxyethyl(meth)acrylate (this abbreviation means 2-hydroxyethylacrylate or 2-hydroxyethylmethacrylate, and similar denotations are used hereinafter), 2- or 3-hydroxypropyl(meth)acrylate, 4-hydroxybutyl(meth)acrylate, 5-hydroxypentyl(meth)acrylate, 6-hydroxyhexyl(meth)acrylate, 10-hydroxydecyl(meth)acrylate; dialkyleneglycolmono(meth)acrylates such as diethyleneglycolmono(meth)acrylate, triethyleneglycolmono(meth)acrylate, tetraethyleneglycolmono(meth)acrylate, polyethyleneglycolmono(meth)acrylate, dipropyleneglycolmono(meth)acrylate, polypropyleneglycolmono(meth)acrylate; 1,2- or 1,3- or 2,3-dihydroxypropyl(meth)acrylate, 2-hydroxypropyl-1,3-di(meth)acrylate, 3-hydroxypropyl-1,2-di(meth)acrylate, N-(meth)acryloyl-1,2-dihydroxypropylamine, N-(meth)acryloyl-1,3-dihydroxypropylamine; and addition products of phenols with glycidyl(meth)acrylate such as 1-phenoxy-2-hydroxy-propyl(meth)acrylate, 1-naphthoxy-2-hydroxypropyl-(meth)acrylate and bisphenol-A-diglycidyl(meth)acrylate. 2-Hydroxyethyl(meth)acrylate and 2-hydroxypropyl(meth)acrylate are particularly suitable among them.

Two or more kinds of these compounds having hydroxy groups can be used together, if desired.

The blending amounts of above-described compounds having hydroxy group and polymerizable unsaturated group are generally in the range of 5-90% by weight, preferably 10-70% by weight and more preferably 20-60% by weight, and the amounts of less than 5% by weight or more than 90% by weight cause deterioration in adhesive property.

The compounds having acidic group and polymerizable unsaturated group which are used in this invention are polymerizable monomers, oligomers or polymers having polymerizable unsaturated group such as acryloyl group, methacryloyl group, vinyl group, allyl group and the like together with acidic group such as carboxyl group, phosphoric acid group, acid anhydride residues, acid-amide groups and the like, the monomers being particularly preferable among them.

Examples of the polymerizable monomers having carboxy group are monocarboxylic acids, dicarboxylic acids, tricarboxylic acids or tetracarboxylic acids and their derivatives such as acrylic acid, methacrylic acid, 1,4-di(meth)acryloxyethyl-pyromellitic acid, 6-(meth)acryloxyethylnaphthalene-1,2,6-tricarboxylic acid, N,O-di(meth)acryloxy-tyrosine, O-(meth)acryloxytyrosine, N-methacryloxytyrosine, N-(meth)acryloxyphenylalanine, N-(meth)acryloyl-p-aminobenzoic acid, N-(meth)acryloyl-o-aminobenzoic acid, N-(meth)acryloyl-5-aminosalicylic acid, N-(meth)acryloyl-4-aminosalicylic acid, 4-(meth)acryloxyethyl trimellitic acid, 4-(meth)acryloxybutyl trimellitic acid, 4-(meth)acryloxyhexyl trimellitic acid, 4-(meth)acryloxydecyl trimellitic acid, 4-acryloxybutyl trimellitic acid, 2-(meth)acryloyloxybenzoic acid, 3-(meth)acryloyloxybenzoic acid, 4-(meth)acryloyloxybenzoic acid, addition product of 2-hydroxyethyl(meth)acrylate with maleic anhydride, p-vinylbenzoic acid, o-methacryloxy-tyrosinamide, N-phenylglycineglycidyl(meth)acrylate, N-(p-methylphenyl)glycineglycidyl-(meth)acrylate, 11-methacryloxy-1,1-undecane dicarboxylic acid, 4-[(2-hydroxy-3-methacryloyloxypropyl)amino]phthalic acid, 5-[(2-hydroxy- 3-methacryloyloxypropyl)amino]isophthalic acid, 3-[N-methyl-N-(2-hydroxy-3-methacryloyloxypropyl)amino]phthalic acid, 4-[N-methyl-N-(2-hydroxy-3-methacryloyl-oxypropyl)amino]phthalic acid, a reaction product of pyromellitic acid dianhydride and 2-hydroxyethyl(meth)acrylate in 1:2 molar ratio, maleic acid and the like. 4-Acryloxy-ethyltrimellitic acid, 4-methacryloxyethyltrimellitic acid and a reaction product of pyromellitic acid dianhydride and 2-hydroxyethyl(meth)acrylate in 1:2 molar ratio are particularly preferable among them.

Radically polymerizable monomers having hydroxyl group and carboxylic group in one molecule are also included in the polymerizable monomers containing acidic groups, especially carboxylic groups, as described in the above examples.

Polymerizable monomers containing phosphoric acid or phosphonic acid groups are suitable for the polymerizable monomers containing phosphoric groups, examples of them being bis[2-(meth)acryloxyethyl]phosphoric acid, [2-(meth)acryloxyethylphenyl]phosphoric acid, 10-(meth)acryloyloxydecyl dihydrogen phosphate, 6-(meth)acryloyloxyhexyl dihydrogen phosphate, vinylphosphonic acid and p-vinylbenzylphosphonic acid. The other examples are polymerizable monomers having thiophosphoric acid group.

Examples of the polymerizable monomers having acid anhydride residues are as follows; 4-(meth)acryloxyethyltrimellitic acid anhydride, 6-(meth)acryloxyethylnaphthalene-1,2,6-tricarboxylic acid anhydride, 6-(meth)acryloxyethylnaphthalene-2,3,6-tricarboxyllic acid anhydride, 4-(meth)acryloxyethylcarbonylpropionoyl-1,8-naphthalic acid anhydride and 4((meth)acryloxyethylnaphthalene-1,8-tricarboxyllic acid anhydride.

Two or more kinds of the above described polymerizable compounds having acidic groups can be used together, if desired.

The blending amounts of the polymerizable compounds having acidic groups are generally in the range of 1-90% by weight, preferably 0.5-60% by weight, and the amount of less than 0.1% by weight causes deterioration in adhesive property while the amounts of more than 90% by weight bring about difficulty in solubility or decrease in adhesive property.

The curing agents conventionally used for initiators and accelerators for polymerization or photopolymerization are also suited for the curing agents to be used in this invention.

Examples of initiators for polymerization, accelerators for polymerization and the other curing agents are organic peroxides, amines and barbituric acid or derivatives thereof, respectively.

Trialkylborones or their oxides are also included in the examples.

Initiators for photopolymerization are initiators for ultraviolet light curing or visible light-curing, and examples of them are organic nitrogen compounds, particularly amines.

The following compounds are the examples of organic peroxides: benzoyl peroxide, 4,4'-dichlorobenzoyl peroxide, 2,4-dichlorobenzoyl peroxide, dilauryl peroxide, methylethylketone peroxide, t-butylperoxymaleic acid and succinic acid peroxide. t-Butylperoxymaleic acid, succinic acid peroxide, benzoyl peroxide and 4,4'-dichlorobenzoyl peroxide are particularly suitable examples among them.

The compounds represented by the following general formula are the examples of the amines;

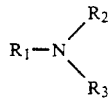

[wherein $R_1$-$R_3$ denote independently hydrogen atom, alkyl groups having 1-10 carbon atoms or cycloalkyl groups having 6-12 carbon atoms which may have substituents (hydroxyl group, (meth)acryloyl groups and the like, for example), or phenyl groups which may have substituents (halogens, alkyl groups having 1-10 carbon atoms, hydroxyl group, (meth)acryloyl group and the like, for example) provided that the groups $R_1$-$R_3$ do not denote hydrogen atom at the same time].

Other amines such as cyclic amines or divalent or more of amines such as diamines may be used.

Examples of these kinds of amines are n-butylamine, propylamine, pentylamine, hexylamine, dimehylamine, diethylamine, dipropylamine, di-n-butylamine, dipentylamine, trimethylamine, triethylamine, tripropylamine, tri-n-butylamine, tripentylamine, trihexylamine, phenylethylamine, ethylenamine, tetramethylenamine, N,N-dimethylaminoethylmethacrylate, N,N-diethylaminoethylmethacrylate, monoethanolamine, N-methyldiethanolamine, triethanolamine, aniline, methylaniline, dimethylaniline, diphenylamine, toluidine, anicidine, N,N-dimethyl-m-anicidine, N,N-dimethyl-p-anicidine, N,N-dimethyl-m-aminophenol, N,N-diethyl-m-aminophenol, N,N-diethyl-p-anicidine, p-propoxy-N,N-dimethylaniline, p-hexyloxy-N,N-dimethylaniline, p-butoxy-N,N-dimethylaniline, chloroaniline, bromoaniline, dimethyl-p-toluidine, N,N-di(2-hydroxyethyl)-p-toluidine, p-aminophenylmethacrylate, N,N-dimethylaminophenyl methacrylate, N,N-di(2-hydroxyethyl)phenylmethacrylate, p-(β-hydroxy-γ-methacryloxypropoxy)phenylamine, N,N-di(2-hydroxyethyl)-phenylglycidyl(meth)acrylate, N-methylmorpholine, imidazole, 1-methylimidazole, 2-methylimidazole, 2-methyl-4-methylimidazole, ethylenediamine, methylenedianiline, phenylenediamine, N,N-bis(hydroxyethyl)diethylenetriamnie, N,N-bis(hydroxyethyl)triethylenetetramine, 3-amino-1,2-propanediol, D,L-1-amino-2-propanol, 2-amino-4-phenylphenol, 2-amino-2-phenylethanol, L-2-amino-1-propanol, 3-amino-1-propanol, 2-anilinoethanol, N,N-dihydroxy-ethylaniline, o- or p-aminophenethyl alcohol, 5-amino-1-pentanol, 5-amino-2-methylphenol, 2-amino-5-methylphenol; aminobenzoic acid esters such as methyl p-aminobenzoate, ethyl p-aminobenzoate, butyl p-aminobenzoate, propyl p-aminobenzoate, isopropyl p-aminobenzoate, ethyl p-(N,N-dimethylamino)benzoate and isopropyl p-(N,N-dimethylamino)benzoate. N,N-di(2-hydroxydiethyl)-p-toluidine, N,N-dimethylaminoethylmethacrylate, p-aminophenylmethacrylate, p-(β-hydroxy-γ-methacryloxypropoxy)phenylamine, triethanolamine, monoethanolamine, isopropyl p-(N,N-dimethylamino)benzoate and ethyl p-aminobenzoate are the suitable examples among them.

The compounds represented by the following formula are the examples of barbituric acid or derivatives thereof:

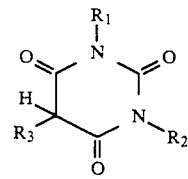

(wherein $R_1$ and $R_2$ may be the same or different with each other and denote hydrogen atom or aliphatic, aromatic, alicyclic or heterocyclic residues which may have substituents such as halogen atoms, alkyl groups, alkoxy groups, allyl groups or cyclohexyl group).

The following compounds are the examples of these compounds: barbituric acid, 1,3-dimethylbarbituric acid, 1-methylbarbituric acid, 1,3-diphenylbarbituric acid, 5-(n-butyl)barbituric acid, 1,5-dimethylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl5-n-butylbarbituric acid, 1,3-dimethyl-5-secbutylbarbituric acid, 1,3-dimethyl-5-isobutylbarbituric acid, 1,3-dimethyl-5-tert-butylbarbituric acid, 1,3-dimethyl-5- cyclopentylbarbituric acid, 1,3-dimethyl-5-cyclohexylbarbituric acid, 1,3-dimethyl-5phenylbarbituric acid, 1-benzyl-5-phenylbarbituric acid, 1-cyclohexyl-5-ethylbarbituric acid and their salts (particularly salts of alkali metals or alkaline earth metals).

The other examples of barbituric acid derivatives are 5-aminobarbituric acid, 2-chlorobarbituric acid, thiobarbituric acid derivatives such as 1,3,5-trimethyl-2-thiobarbituric acid, 5-butyl-2-thiobarbituric acid and their salts (particularly salts of alkali metals or alkaline earth metals).

Particularly suitable barbituric acid derivatives are 5(n-butyl)barbituric acid, 1,3,5-trimethylbarbituric acid, 1,3-dimethyl-5-isobutylbarbituric acid, 1-benzyl-5-phenylbarbituric acid, 1-cyclohexyl-5-ethylbarbituric acid and 1,3,5-trimethyl-2-thiobarbituric acid.

Examples of trialkylborone or their oxides are tri-n-butylborone, tri-n-amylborone, triisoamylborone, tri-sec-amylborone, triethylborone, tripropylborone, triisopropyl-borone or their derivatives which are oxidized partially.

Sensitizers for ultraviolet or visible light such as benzoin methylether, benzoin ethylether, benzoin isopropylether, benzoin, benzophenone, 2-chlorothioxanthone, 2-hydroxy-3-(3,4-dimethyl-9H-thioxanthene-2-yloxy)-N,N,N-trimethyl-1-propane ammonium chloride, 9,10-anthraquinone, camphorquinone, benzyl, 4,4'-dicyclo-benzyl and diacetyl are the examples of initiators for photopolymerization.

Examples of accelerators for photopolymerization are N,N-dimethyl-p-toluidine, N,N-di(2-hydroxyethyl)-p-toluidine, triethylamine, trihexylamine, 2-dimethylamino-ethanol, N-methylethanolamine, N,N-dimethylaminoethyl-methacrylate and N,N-diethylaminomethacrylate.

Two or more kinds of the above described curing agents may be used, if necessary.

The blending amounts of the curing agent are in the range of 0.01-30% by weight, preferably 0.05-10% by weight and more preferably 0.1-5% by weight. When the amounts are less than 0.01% by weight, adhesive property tends to decrease while it is also decreased when the amounts are more than 30% by weight.

Besides the components described above, appropriate amounts of polymerizable compounds without hydroxyl group and acidic groups, i.e, urethane (meth)acrylates such as an adduct of 1,1,3-trimethylhexamethylene diisocyanate and 2-hydroxyethylmethacrylate in 1:2 molar ratio, an adduct of isophorone diisocyanate and 2-hydroxyethylmethacrylate in 1:2 molar ratio, and Bisphenol A-dimethacrylate, ethylenglycoldimethacrylate, trietyleneglycoldimethacrylate, polyethylenglycoldimethacrylate, N-vinyl-pyrolidone and Methoxypolyethylenglycolmonomethacrylate may be blended, if desired. The blending amounts of the polymerizable compounds without hydroxyl group and acidic groups are in the ranges of 0-90% by weight.

Besides the components described above, appropriate amounts of organic solvents, i.e. alcohols such as ethyl alcohol, isopropyl alcohol, propylalcohol and the like, ketones such as acetone and the like, aldehydes such as glutaraldehyde, formaldehyde and the like, or tetrahydrofurane may be blended, if desired, to the primer composition according to the present invention in order to adjust the viscosity of the composition or solubility of the components of the composition. The blending amounts of the organic solvents are in the range of 0-90% by weight. Hydroquinone, hydroquinone monomethylether, hydroxymethoxybenzophenone or butylated hydroxytoluene may be blended appropriately as a stabilizer for the shelf life of the composition.

The composition according to the present invention can be used by dividing the components of the composition into two or more portions. When the components of a curing agent are composed of initiators and accelerators, for example, they can be divided into two or more portions so that they can be subjected to use after mixing. Even when the component of the curing agent is composed of one kind of agent, it can be divided into two portions for use. Methods for mixing the portions are possible to be selected appropriately. The method for mixing the portions in a small plate by the dentist immediately before use, and the method for mixing the portions in cavities of the patient's teeth for adhesion are exemplified. These dividing methods of the components can be selected appropriately from their combinations. For the primer composition comprising (i) water, (ii) a compound having hydroxyl group and polymerizable unsaturated group, (iii) a compound having acidic group and polymerizable unsaturated group, and (iv) a curing agent, the following combinations are exemplified; (i) and (ii) for solution A and (iii) and (iv) for solution B; (i) and (ii) for solution A and (ii), (iii) and (iv) for solution B; (i), (ii) and (iv) for solution A and (ii) and (iii) for solution B; (i) for solution A and (ii), (iii) and (iv) for solution B; (i) and (iii) for solution A and (ii) and (iv) for solution B; (i), (ii) and (iii) for solution A and (iv) for solution B; or (i), (ii) and (iv) for solution A and (ii), (iii) and (iv) for solution B (one component can be amines and another component can be a curing agent in (iv) in some cases).

The present invention will be illustrated by the following examples, but it is not restricted to these examples.

EXAMPLES 1-5 AND COMPARATIVE EXAMPLES 1-6

Eleven primers were prepared from ion-exchange water, 2-hydroxyethylmethacrylate (2-HEMA), 4-acryloxyethyl trimellitic acid (4-AET), 4-acryloxyethyl trimellitic acid anhydride (4-AETAA), bis(2-methacryloxyethyl)phosphoric acid (BMEPA), N,N-di(hydroxyethyl)-p-toluidine (N,N-DEPT), 4,4'-dichlorobenzoylperoxide (p-Cl-BPO) and glutaraldehyde according to the formulation listed in Table 1.

A powder component of a resin cement was prepared by mixing silane-treated silica (75 parts by weight), silane-treated barium sulfate (25 parts by weight), N,N-di-(2-hydroxyethyl)-p-toluidine (0.1 part by weight) and 1-benzyl-5-phenyl-barbituric acid (1.0 part by weight). A liquid component of the resin cement was prepared by mixing a reaction product of 1,1,3-trimethylhexamethylene diisocyanate and 2-hydroxyethylmethacrylate in 1:2 molar ratio (60 parts by weight), triethyleneglycol dimethacrylate (28 parts by weight), 2-hydroxyethylmethacrylatte (7 parts by weight), 4-acryloxyethyl trimellitic acid (5 parts by weight), benzoyl peroxide (0.3 part by weight) and butylated hydroxytoluene (0.05 part by weight). The resin cement was prepared immediately before use by mixing the both components in a powder/liquid ratio of 3.5/1.0.

Silane treatment of the filler (silica and barium sulfate) was carried out by using γ-methacryloxypropyltrimethoxysilane according to the following conventional acetic acid method. One hundred parts by weight of the filler was added to 100 parts by weight of a solution which was prepared by dissolving γ-methacryloxypropyltrimethoxysilane into 0.1% of aqueous acetic acid solution to form 2.0% by weight in concentration. After air-drying this slurry, surface treatment of the filler was carried out by subjecting the silane-treated filler to a heat treatment at 80° C. for 2 hours, followed by an additional heat treatment at 120° C. for 30 minutes.

Adhesive strength was determined by a shear bond test between a bovine dentin and the resin cement. Freshly extracted bovine anterior teeth was freeze-stored in distilled water and was defrosted immediately before use. The bovine teeth were mounted in epoxy resin and the surface of the dentin was polished by using a water-proof abrasive paper (#600) to make the surface smooth. After polishing the bovine dentin, the surface of the dentin was treated by respective primers listed in Table 1 in a rubbing manner for 60 seconds. After drying the teeth, the mixed slurry of the resin cement was cured and made to adhere onto the surface of the dentin by using a separable plastic mould of 4 mm in inner diameter and 2 mm in height. Thirty minutes after the curing of the cement, the adhered test samples were immersed in distilled water at 37° C. for 24 hours and then a adhesive strength under a compressive shearing force was measured by using a Shimadzu autograph AG-5000B at a cross-head speed of 1 mm/min. All the tests described above and hereinafter were carried out at room temperature of 23°±2° C. The results are shown in Table 1.

served in the Comparative Example 6 in comparison with the result in the Comparative Example 7. It is apparent from the results in the Comparative Examples 1–5 (13.4 to 34.7 kgf/cm$^2$) that any lack of the components of the primer composition according to the present invention results in a remarkable decrease in the adhesive strength. It was made clear from these results that an excellent adhesive strength against the dentin without acid treatment can be obtained by an interaction among ion-exchange water, 2-HEMA, 4-AET and N,N-DEPT which are the basic constituents of this invention.

When 4-AETA having an acid anhydride group (Example 2) or BMEPA having phosphoric acid group (Example 3) was used as a polymerizable monomer having acidic group instead of 4-AET in which the acidic group is a carboxyl group, or when a peroxide was used for the curing agent (Example 4), and when the blending amounts of the components constituting this invention were varied (Example 5), the values of 70.9–90.8 kgf/cm$^2$ were obtained which are significantly higher than the values obtained in the Comparative Examples 1–7.

Adhesive strength under shearing force between the bovine enamel without acid etching treatment and the resin cement prepared by way of test was measured after immersing the test sample in distilled water at 37° C. for one day, wherein the compositions obtained in the Examples 1 and 2 were used as a primer. The value obtained by using the composition according to the

TABLE 1

| Components[1] & | Examples | | | | | Comparative Examples | | | | | | |
|---|---|---|---|---|---|---|---|---|---|---|---|---|
| Adhesive strength | 1 | 2 | 3 | 4 | 5 | 1 | 2 | 3 | 4 | 5 | 6 | 7 |
| Ion-exchange water | 40 | 40 | 40 | 40 | 50 | 40 | 40 | 40 | — | 100 | 40 | No primer |
| 2-HEMA | 60 | 60 | 60 | 60 | 50 | 60 | 60 | 60 | 100 | — | 60 | |
| 4-AET | 7 | — | — | 7 | 10 | — | 7 | — | 7 | 7 | — | |
| 4-AETA | — | 7 | — | — | — | — | — | — | — | — | — | |
| BMEPA | — | — | 7 | — | — | — | — | — | — | — | — | |
| N,N-DEPT | 0.6 | 0.6 | 0.6 | — | 0.6 | — | — | 0.6 | 0.6 | 0.6 | — | |
| P—Cl.BPO | — | — | — | 0.15 | — | — | — | — | — | — | — | |
| Glutaraldehyde | — | — | — | — | — | — | — | — | — | — | 7 | |
| BHT | — | — | — | 0.01 | — | — | — | — | — | — | — | |
| Adhesive strength (kgf/cm$^2$) | 127.6 | 70.9 | 83.2 | 90.8 | 78.4 | 13.4 | 34.4 | 25.7 | 34.7 | 22.1 | 30.9 | 33.5 |

(Note) 1. Unit of the blending amounts of the components is part(s) by weight.

As apparent from Table 1, in the case of Example 1 in which a primer comprising ion-exchange water, 2-HEMA, 4-AET and N,N-DEPT, which are the components constituting the present invention, was used, a value of 127.6 kgf/cm$^2$ was obtained for adhesive strength under compressive shearing force between the bovine dentin without being subjected to an acid etching (hereinafter, abbreviated as a dentin without acid etching) and the resin cement prepared by way of test. In the Comparative Examples 1–7 wherein the compositions which are out of the range of this invention were used, on the other hand, the results showed very low values. In the Comparative Example 7 in which no primer was used, the value was 33.5 kgf/cm$^2$ while a four times higher value of the adhesive strength was obtained in the case in which the bovine dentin was subjected to a primer treatment according to this invention. In the Comparative Example 6 in which a conventional composition comprising ion-exchange water, 2-HEMA and glutaraldehyde was used, a value of 30.9 kgf/cm$^2$ was obtained for the dentin without acid treatment, showing that the value was significantly low compared with that obtained by the composition according to this invention. No primer effect was ob- Example 1 was 187.7 kgf/cm$^2$. When the bovine enamel was subjected to an etching treatment with phosphoric acid instead of the primer treatment of this invention, adhesive strength of 208.0 kgf/cm$^2$ was obtained. These results indicate that the substantially same adhesive strength as that obtained by the etching treatment with phosphoric acid can be obtained by using the primer according to this invention. The adhesive strength of the resin cement to the bovine enamel which was not subjected to primer or acid treatment was 56 kgf/cm$^2$. From the results described above, it was made clear that the primer compositions according to this invention are also effective for increasing the adhesive property to the enamel which was not subjected to an etching treatment with an acid.

EXAMPLES 6 AND 7 AND COMPARATIVE EXAMPLES 8 AND 9

Adhesive primers were prepared according to the formulations shown in Table 2 and adhesive strength under shearing force between the dentin without acid treatment and resin cements which were prepared by way of test in the Examples 1-5 and the Comparative Examples 1-7) was measured according to the same manner as that described in the aformentioned Examples. The result are shown in Table 2.

TABLE 2

| Components[1] & Adhesive strength | Example | | Comparative Example | |
|---|---|---|---|---|
| | 6 | 7 | 8 | 9 |
| Ion-exchange water | 40 | 40 | 40 | 40 |
| 2-HEMA | 60 | 60 | 60 | 60 |
| 4-AET | 7 | — | — | 7 |
| MEPP[2] | — | 7 | — | — |
| N,N-DEPT | 0.6 | 0.6 | — | — |
| BBA[3] | 0.4 | — | — | — |
| NaCl | — | — | 0.6 | 0.6 |
| Adhesive strength to dentin (kgf/cm$^2$) | 95.2 | 112.7 | 42.3 | 65.7 |

(Note)
[1]Unit of the blending amounts of the components is part(s) by weight.
[2]MEPP: Methacryloxyethylphenyl phosphoric acid
[3]BBA: 5-(n-butyl)barbituric acid As apparent from Table 2, significantly higher adhesive strength to the dentin was obtained when the primer composition according to this invention was used (Examples 6 and 7) than that in the Comparative Examples 8 and 9 wherein salt of a mineral acid is blended with the mixture of water and 2-hydroxyethylmethacrylate or the mixture of water, 2-hydroxyethylmethacrylate and 4-acryloxyethyl trimellitic acid.

EXAMPLE 8

A primer was prepared by mixing 35 parts by weight of distilled water, 60 parts by weight of 2-hydroxyethylmethacrylate, 5 parts by weight of 4-methacryloxyethyl trimellitic acid, 0.6 part by weight of camphorquinone and 0.8 part by weight of N,N-dimethylaminoethylmethacrylate.

A powder compoment of a chemically and photochemically curable resin cement was prepared by mixing 75 parts by weight of silane-treated silica, 25 parts by weight of silane-treated barium sulfate, 5 parts by weight of 4-acryloxyethyl trimellitic acid and 0.3 part by weight of benzoyl peroxide. A liquid compoment of said resin cement was prepared by mixing 40 parts by weight of a reaction product of isophorone diisocyanate and 2-hydroxyethyl-methacrylate in 1:2 molar ratio, 10 parts by weight of bisphenol A-diglycidyl-methacrylate, 30 parts by weight of triethyleneglycoldimethacrylate, 10 parts by weight of ethyleneglycoldimethacrylate, 10 parts by weight of 2-hydroxyethylmethacrylate, 0.6 part by weight of camphorquinone, 0.5 part by weight of N,N-dimethylaminoethylmethacrylate and 0.5 part by weight of N,N-dimethyl-p-toluidine. The curable resin cement was prepared immediately before use by mixing the both components in a power/liquid ratio of 3.2/1.0.

For measuring the adhesive strength under shearing force between the dentin without acid treatment and resin cement, a test sample was prepared according to the method described in the Example 1 and a visible light beam was irradiated for 30 seconds over the surface of the applied resin cement by using the Shofu Daylight Lamp II (Shofu Inc.). The measurement was carried out under the same condition as that used in the Example 1.

The adhesive strength under shearing force between the dentin without acid treatment and the resin cement was 110.2 kgf/cm$^2$, said value being significantly higher than the value of 10.7 kgf/cm$^2$ obtained by using no primer described above.

These results indicate that a light-cure agent is also effective as a curing agent for increasing the adhesive strength.

EXAMPLE 9

One solution (Solution A) of two liquids type primer was prepared by mixing 80 parts by weight of ion-exchange water, 20 parts by weight of 2-hydroxyethylmethacrylate and 0.8 part by weight of N,N-di( 2-hydroxyethyl)-p-toluidine. The other solution (Solution B) was prepared by mixing 100 parts by weight of 2-hydroxyethylmethacrylate, 15 parts by weight of 4-methacryloxyhexyl trimellitic acid, 0.5 part by weight of benzoyl peroxide and 0.08 part by weight of butylated hydroxytoluene. The primer was prepared immediately before use by mixing equal amounts of solutions A and B. Adhesive strengths under shearing force to a dentin, an enamel or a glass ionomer cement [Shofu Base Cement (Shofu Inc.) which was used after 1 hour from curing] without acid treatment were determined by using the resin cement used in the Example 1 in the manner described in the Example 1. The results are listed in Table 3.

TABLE 3

| | Dentin without acid treatment | Enamel without acid treatment | Glass ionomer cement without acid treatment |
|---|---|---|---|
| Adhesive strength[1] under shearing force | 83.3 kgf/cm$^2$ | 158.8 kgf/cm$^2$ | 140.7 kgf/cm$^2$ |

(Note) [1]The adhesive strength shows the results after the test sample was immersed in water at 37° C. for 24 fours.

EXAMPLE 10

Adhesive strength between the dental light-cure composite resin [Shofu LITE-FIL P (Shofu Inc.)] and the dentin or glass ionomer cement without acid treatment was evaluated by using the composition according to this invention as a primer. A one liquid type light-cure bonding agent was prepared by mixing 60 parts by weight of a reaction product between isophorone diisocyanate and 2-hydroxyethylmethacrylate in 1:2 molar ratio (IPDI-2-HEMA), 30 parts by weight of triethyleneglycoldimethacrylate, 5 parts by weight of 2-hydroxyethylmethacrylate, 5 parts by weight of ethyleneglycoldimethacrylate, 0.8 part by weight of dl-camphorquinone, 1.0 part by weight of N,N-dimethylaminoethylmethacrylate and 0.05 part by weight of butylated hydroxytoluene.

Solution A prepared in the Example 9 was used as one solution of two liquids type primer for the dentin or the glass ionomer cement without acid treatment, and the other solution (solution B) was prepared by mixing 100 parts by weight of 2-hydroxyethylmethacrylate, 14 parts by weight of 4-acryloxyethyl trimellitic acid and 0.01 part by weight of butylated hydroxytoluene. Equal amounts of solution A and B were mixed to prepare the primer. The dentin or the glass ionomer cement was treated with the primer in a rubbing manner and was dried after 60 seconds. After drying, the one liquid type light-cure bonding agent was applied to the dentin or the glass ionomer cement by using a small painting brush and visible light was irradiated on the surface thereof by means of Shofu Daylight Lamp-II (Shofu Inc.) for 30 seconds. A plastic mould (inner diameter: 4 mm, height: 2 mm) was fixed to the dentin or the glass ionomer cement. Shofu LITE-FIL-P (Shofu Inc.) was filled into the plastic mould and visible light was irradiated for 30 seconds on the surface thereof by the same method as described above. The obtained test samples were immersed in water at 37° C. for 1 day (0th cycle) and then Thermal Cycling Tests (1 cycle: immersed in water at 4° C. for 1 minute⇌immersed in water at 60° C. for 1 minute) in order to evaluate a durability concerning the adhesive strength. The test samples were subjected to 0, 2000, and 5000 times of the Thermal Cycling Tests and the adhesive strength under shearing force after each cycle was measured. The results are shown in Table 4.

TABLE 4

| Test sample | Adhering agent | Adhesive strength (kgf/cm$^2$) under shearing force | | |
|---|---|---|---|---|
| | | 0th cycle | 2000th cycle | 5000th cycle |
| Dentin without acid treatment | Composite resin | 176.6 *D | 163.8 *D | 157.5 *D |
| Glass ionomer cement without acid treatment | Composite resin | 187.5 *G | 194.4 *G | 188.2 *G |

(Note)
*D: Cohesive failure in dentin
*G: Cohesive failure in glass ionomer cement No adhesive strength (0 kgf/cm$^2$) was observed for the dentin without acid treatment by using the one liquid type light-cure bonding agent and Shofu LITE-FIL-P instead of using the composition according to this invention prepared by mixing the solutions A and B. On the contrary, when the primer prepared by mixing the solutions A and B, the results listed in Table 4 were obtained and Cohesive failure in the dentin or glass ionomer cement was observed. These results show that the primer composition according to this invention brings about an extremely high and durable adhesive effect against the substrate to be adhered.

EXAMPLES 11–17

Adhesive property between a dental light-cure composite resin of Shofu LITE-FIL-P (Shofu Inc.) and a dentin without acid treatment was evaluated by using the composition according to this invention as a primer. A one liquid type light-cure bonding agent was prepared by mixing 50 parts by weight of a reaction product of 1,3,5-trimethylhexamethylene dimethacrylate and 2-hydroxyethylmethacrylate in 1:2 molar ratio, 35 parts by weight of triehtyleneglycoldimethacrylate, 10 parts by weight of ethyleneglycoldimethacrylate, 5 parts by weight of 2-hydroxyethylmethacrylate, 0.8 part by weight of dl-camphorquinone, 1.0 part by weight of N,N-dimethylaminoethylmethacrylate and 0.05 part by weight of butylated hydroxytoluene.

A bovine dentin polished by water-proof abrasive paper (#600) was treated with the primer in a rubbing manner for 60 seconds, then air-dried for 20 seconds. The dentin was then coated with the above-described one liquid type light-cure bonding agent by using a small painting brush, and visible light was irradiated for 30 seconds by means of Shofu Daylight Lamp II (Shofu Inc.). A plastic mould (inner diameter: 4 mm, height: 2 mm) was fixed to the dentin. Shofu LITE-FIL-P was filled into the mould and visible light was irradiated for 30 seconds from the top face of the mould. Adhesive strength under compressive sharing force of the adhered test sample was measured after immersing the test sample in water at 37° C. for 24 hours. A primer was prepared by blending 7 parts by weight of 4-acryloxyethyl trimellitic acid and 0.6 part by weight of N,N-di(2-hydroxyethyl)-p-toluidine with water/2-hyrdoxyethylmethacrylate (2-HEMA) in an amount shown in Table 5. The results of the measured adhesive strength under compressive shearing force of the adhered test samples when respective primers were used are shown in Table 5.

TABLE 5

| | Water (parts by weight) | 2-HEMA (parts by weight) | Adhesive strength under shearing force (kgf/cm$^2$) |
|---|---|---|---|
| Comparative Example 10 | 100 | 0 | 29.4 #D |
| Example 11 | 80 | 20 | 79.6 |
| Example 12 | 70 | 30 | 82.8 |
| Example 13 | 60 | 40 | 132.9 *D |
| Example 14 | 50 | 50 | 216.3 *D |
| Example 15 | 40 | 60 | 247.0 *D |
| Example 16 | 30 | 70 | 98.7 |
| Example 17 | 20 | 80 | 115.4 *D |
| Comparative Example 11 | 0 | 100 | 33.8 #D |
| Comparative Example 12 | No primer is used | | 0 |

(Note)
*D: Cohesive failure in dentin
D: Adhesive failure in dentin

EXAMPLES 18–31

Adhesive strength under shearing force to the dentin without acid treatment was evaluated by using a similar method as described in the Example 11–17, wherein Shofu LITE-FIL-P (Shofu Inc.), the one liquid type light-cure bonding agent used in the Examples 11–17 and a primer composition was prepared by blending 4-acryloxyethyl trimellitic acid (4-AET) with 40 parts by weight of ion-exchange water and 60 parts by weight of 2-hydroxyethylmethacrylate in an amount listed in Table 6 were employed. N,N-Di(2-hydroxyethyl)-p-toluidine was added to the primer composition in amount of 0.6 part by weight based on the total amount of said three components. The result of the measured adhesive strength under compressive shearing force of the adhered test samples when respective primers were used are shown in Table 6.

TABLE 6

| | 4-AET (part(s) by weight) | Adhesive strength under shearing force (kgf/cm$^2$) |
|---|---|---|
| Comparative Example 13 | 0 | 57.3 #D |
| Example 18 | 0.5 | 100.6 |
| Example 19 | 1.0 | 104.3 |
| Example 20 | 2.5 | 199.5 *D |
| Example 21 | 5.0 | 200.3 *D |
| Example 22 | 7.0 | 247.0 *D |
| Example 23 | 10.0 | 165.5 *D |
| Example 24 | 15.0 | 133.8 *D |
| Example 25 | 20.0 | 145.7 *D |
| Example 26 | 30.0 | 186.7 *D |
| Example 27 | 60.0 | 258.1 *D |
| Example 28 | 90.0 | 251.5 *D |

TABLE 6-continued

|  | 4-AET (part(s) by weight) | Adhesive strength under shearing force (kgf/cm$^2$) |
| --- | --- | --- |
| Example 29 | 100.0 | 216.6 *D |
| Example 30 | 120.0 | 303.0 *D |
| Example 31 | 130.0 | 175.1 *D |

(Note)
D: Adhesive failure in dentin
*D: Cohesive failure in dentin

As apparent from Table 6, about 2–6 times higher adhesive strength for the dentin was obtained by using the primers according to the Examples 18–31, in which the primers comprise the monomer having acidic group (4-AET), than that obtained by using the primer which does not comprise said this monomer (Comparative Example 13). A particularly high adhesive strength of 303 kgf/cm$^2$ was obtained in the Example 30. In the Example 30, there was the adhered test sample which shows adhesive strength of 472.8 kgf/cm$^2$ (failure in dentin), said value being an amazingly high adhesive strength exceeding the tensile strength of the natural dentin [420 kgf/cm$^2$: Dental Engineering, Vol. 70, p. 42 (1984)].

EXAMPLES 32–40

Adhesive strength under shearing force of a dental light-cure composite resin to the dentin without acid treatment was evaluated according to the method described in the Examples 11–17, wherein composition according to this invention as a primer, and Shofu LITE FIL-P (Shofu Inc.), the one liquid type light-cure bonding agent which used in the Example 11–17 and a primer composition prepared by blending 40 part by weight of ion-exchange water, 60 parts by weight of 2-hydroxyethylmethacrylate and 7 parts by weight of 4-acryloxyethyl trimellitic acid with N,N-di(2-hydroxyethyl)-p-toluidine (N,N-DEPT) in an amount listed in Table 6 were employed. The result of the measured adhesive strength under shearing force of the adhered test samples when respective primers were used are shown in Table 7.

TABLE 7

|  | N,N-DEPT (part(s) by weight) | Adhesive strength under shearing force (kgf/cm$^2$) |
| --- | --- | --- |
| Comparative Example 14 | 0.0 (0.00 mol %) | 75.2 |
| Example 32 | 0.3 (0.154 mol %) | 218.1 *D |
| Example 33 | 0.6 (0.307 mol %) | 247.0 *D |
| Example 34 | 0.9 (0.462 mol %) | 116.4 *D |
| Example 35 | 1.2 (0.616 mol %) | 117.8 *D |
| Example 36 | 1.5 (0.770 mol %) | 147.3 *D |
| Example 37 | 3.0 (1.540 mol %) | 117.5 *D |
| Example 38 | 6.0 (3.080 mol %) | 126.2 *D |
| Example 39 | 10.0 (5.130 mol %) | 135.3 *D |
| Example 40 | 30.3 (15.4 mol %) | 96.5 |

(Note) The numerals in parentheses in the table denote mole % relative to the mixture of water (40 parts by weight)/2-HEMA (60 parts by weight).
*D: Cohesive failure in dentin

EXAMPLE 41

A primer was prepared by mixing 40 parts by weight of ion-exchange water, 60 parts by weight of 2-hydroxyethylmethacrylate, 10 parts by weight of ethyl alcohol, 1.0 part by weight of N-phenylglycineglycidylmethacrylate and 0.6 part by weight of N,N-di(2-hydroxyethyl)-p-toluidine. Adhesive strength under shearing force to the dentin without acid treatment was evaluated according to the method described in the Examples 11–17, wherein said primer, Shofu LITE FIL-P (Shofu Inc.) and one liquid type light-cure bonding agent used in the Examples 11–17 were employed. Adhesive strength of 102 kgf/cm$^2$ was obtained.

EXAMPLES 42–47

Adhesive strength under shearing force of a dental light-cure composite resin to the dentin without acid treatment was evaluated according to the methods described in the Examples 11–17, wherein Shofu LITE FIL-P (Shofu Inc.), one liquid type light-cure bonding agent used in the Examples 11-17 and a primer composition prepared by blending 40 parts by weight of ion-exchange water, 60 parts by weight of 2-hydroxyethylmethacrylate and 7 parts by weight of 4-acryloxyethyl trimellitic acid with various kinds of amines in an amount listed in Table 8 were employed. The results of the measured adhesive strength under shearing force of the adhered test samples when respective primers were used are shown in Table 8. The amines were blended in the amount of 0.307 mol % relative to the mixture of water (40 parts by weight)/2-HEMA (60 parts by weight).

TABLE 8

|  | Amines | Part(s) by weight (mol %) | Adhesive strength under shearing force (kgf/cm$^2$) |
| --- | --- | --- | --- |
| Example 42 | Monoethanol-amine | 0.19 (0.307) | 133.9 *D |
| Example 43 | Triethanol-amine | 0.46 (0.307) | 199.3 *D |
| Example 44 | DMMA$^1$ | 0.48 (0.307) | 141.1 *D |
| Example 45 | PABE$^2$ | 0.51 (0.307) | 177.9 *D |
| Example 46 | HMPA$^3$ | 1.02 (0.307) | 126.7 *D |
| Example 47 | APM$^4$ | 0.67 (0.307) | 204.6 *D |

(Note)
$^1$N,N-dimethylaminoethylmethacrylate
$^2$Ethyl p-aminobenzoate
$^3$p-($\beta$-Hydroxy-$\gamma$-methacryloxypropoxy) phenylamine
$^4$p-Aminophenylmethacrylate
$^5$*D: Cohesive failure in dentin

EXAMPLE 48

A primer was prepared by mixing distilled water (40 parts by weight), 2-hydroxyethylmethacrylate (60 parts by weight), 4-acryloxyethyl trimellitic acid (7 parts by weight), triethyleneglycol dimethacrylate (3 parts by weight), dl-camphorquinone (0.6 part by weight), N,N-dimethylaminoetylmethacrylate (0.8 part by weight).

One liquid type light-cure bonding agent was prepared by mixing an adduct of 2,2,4-trimethylhexamethlene diisocyanate and 2-hydroxyethylmetacrylate in 1:2 molar ratio (50 parts by weight), triethyleneglycoldimethacrylate (30 parts by weight), ethyleneglycoldimethacrylate (5 parts by weight), 2-hydroxyethylmetacrylate (10 parts by weight), 4-acryloxyethyl trimellitic acid (5 parts by weight), dl-camphorquinone (0.8 part by weight) and N,N-dimethylaminoetylmethacrylate (1.0 part by weight).

A bovine dentin mounted in epoxy resin was polished by using a water-proof abrasive paper (#600), washed with water and dried. The surface of the bovine dentin was rubbed for one minute by means of a piece of sponge impregnated with the primer and then dried with air. The light-cure bonding agent was applied to the surface of the bovine dentin and then visible light was irradiated on said surface for 30 seconds by means of Shofu Daylight Lamp II (Shofu Inc.). A plastic mould (inner diameter: 4 mm, height: 2 mm) was fixed to the bovine dentin and a light-cure composite resin [Shofu LITE-FIL A (Shofu Inc.)] were filled in the plastic mould and then light-cured to form an adhered test sample. The adhered test sample was immersed in distilled water at 37° C. for 24 hours and then subjected to a Shear Bond Test. The adhesive strength of said sample was 210 kgf/cm$^2$.

EXAMPLE 49

An adhered test sample was prepared accoring to the same manner as that described in Example 48 except that 1,2-dihydroxypropylmethacrylate was employed in place of 2-hydroxyethlmethacrylate as an ingredient of a primer. The adhered test sample was subjected to a Shear Bond Test. The adhesive strength of said sample was 225 kgf/cm$^2$.

EXAMPLES 50 AND 51

In order to evaluate the adhesive strength of a PMMA type dental restorative resin "ADFA" (Shofu Inc.) to the dentin, a primer was prepared by mixing 40 parts by weight of distilled water, 50 parts by weight of 2-hydroxyethylmethacrylate, 10 parts by weight of 1,2-dihydroxypropylmethacrylate, 5 parts by weight of 4-methacryloxyethyl trimellitic acid and 0.6 part by weight of N,N-(2-hydroxyethyl)-p-toluidine. The MMA type bonding liner "ACRYL BOND" (Shofu Inc.) in accordance with the instruction and the one liquid type light-cure bonding agent used in the Example 48 were used. The adhesive strength under shearing force between the dentin without acid treatment and "ADFA" was measured according to the method described in the Example 48. The results of the measured adhesive strength of the adhered test samples are shown in Table 9.

TABLE 9

| | Primer | Bonding agent | PMMA resin | Adhesive strength under shearing force (kgf/cm$^2$) |
|---|---|---|---|---|
| Example 50 | Primer of this invention | Acryl bond | ADFA | 124.2 |
| Example 51 | Primer of this invention | One liquid type bonding agent | ADFA | 123.4 |
| Comparative Example 15 | — | Acryl bond | ADFA | 23.6 |
| Comparative Example 16 | — | — | ADFA | 9.6 |

EXAMPLE 52

The dentin without acid treatment was treated with the primer and the one liquid type light-cure bonding agent used in the Example 48 and then the resin cement used in the Example 1 was made to adhere in place of LITE-FIL to the dentin according to the method described in the Example 48. The adhesive strength under shearing force between the dentin and the resin cement measured by the method of the Example 48 was 227 kgf/cm$^2$.

EXAMPLE 53

A composite resin was prepared by mixing silane-treated silica obtained by the method of the Example 1 (50 parts by weight), a reaction product of 2,2,4-trimethylhexamethylene diisocyanate and 2-hydroxyethylmethacrylate in 1:2 molar ratio (27.0 parts by weight), triethyleneglycoldimethacrylate (13 parts by weight), 2-hydroxyethylmethacrylate (5 parts by weight), 4-acryloxyethyl trimellitic acid (4 parts by weight), dl-camphorquinone (0.4 part by weight) and N,N-dimethylaminoethylmethacrylate (0.6 part by weight).

According to the method described in the Example 48, the primer used in the Example 48 was applied on the surface of the dentin and the composite resin was made to adhere directly to the dentin and then the Shear Bond Test was carried out. The adhesive strength under shearing force between the dentin and the composite resin was 140 kgf/cm$^2$.

The same Shear Bond Test as that described above was carried out except that the primer was not applied on the surface of the dentin. The adhesive strength under shearing force between the dentin and the composite resin was 35 kgf/cm$^2$.

EXAMPLE 54

An adhesive PMMA resin consisting of a powder component and a liquid component was prepared. The powder component was prepared by mixing polymethylmethacrylate powder (100 parts by weight), N,N-bis(-hydroxyethyl)-p-toluidine (0.5 part by weight) and 5-buthyl barbituric acid (1.5 parts by weight). The liquid component was prepared by mixing methylmethacrylate (80 parts by weight), triethyleneglycoldimethacrylate (6 parts by weight), 4-acryloxyethylmethacrylate (8 parts by weight), benzyl peroxide (0.3 part by weight) and butylated hydroxy toluene (0.08 part by weight).

According to the method described in the Example 48, the primer used in the Example 49 was applied on the surface of the dentin and the PMMA resin was made to adhere directly to the dentin and then the Shear Bond Test was carried out. The adhesive strength under shearing force between the dentin and the PMMA resin was 178 kgf/cm$^2$.

The primer composition according to this invention is in general a suitable composition as an undercoating for adhering the bonding restorations to the substrates. For example, when dental adhesive restorative materials such as dental resin cements, composite resins, PMMA resins and the like are made to adhere directly or through bonding agents to substrates such as vital hard tissues, especially enamel or dentin of natural teeth, glass ionomer cements and the like, the primer composition imparts a strong and durable adhesive property between the both.

Although the object of this invention is focused on the field of dental medicine, the primer composition according to this invention has a wide variety of applications in other fields such as surgery, orthopaedic surgery, anaplastic surgery and the like.

We claim:

1. A primer composition which comprises (i) 10–55% by weight of water, (ii) 20–60% by weight of the compound having hydroxyl group and polymerizable unsaturated group, (iii) 2.5–60% by weight of the compound having acidic group and polymerizable unsaturated group, and (iv) 0.3–10% by weight of the curing agent.

2. A primer composition according to claim 1, wherein the component (ii) is a polymerizable monomer having acryloyl group, methacryloyl group, vinyl group or acrylic group together with hydroxyl group.

3. A primer composition according to claim 2, wherein the polymerizable monomer is 2-hydroxyethyl (meth)acrylate or 2,3-dihydroxypropyl (meth)acrylate.

4. A primer composition according to claim 2, wherein the component (iii) is a polymerizable monomer having acryloyl group, methacryloyl group, vinyl group or acrylic group together with carboxyl group, phosphoric acid group, acid anhydride residue or acid amide group.

5. A primer composition according to claim 4, wherein the polymerizable monomer is 4-acryloxyethyl trimellitic acid, 4-methacryloxyethyl trimellitic acid, a reaction product of pyromellitic acid dianhydride and 2-hydroxymethacrylate in 1:2 molar ratio or 11-(meth)acryloxy-1,1-undecane dicarboxylic acid.

6. A primer composition according to claim 4, wherein the polymerizable monomer is phosphoric acid, 10-(meth)acryloyloxydecyl dihydrogen phosphate, 6-(meth)acryloyloxyhexyl dihydrogen phosphate or p-vinylbenzylphosphonic acid.

7. A primer composition according to claim 4, wherein the polymerizable monomer is 4-(meth)acryloxy-ethyl trimellitic acid anhydride, 6-(meth)acryloxyethyl-naphthalene-1,2,6-tricarboxylic acid anhydride, 6-(meth)-acryloxyethylnaphthalene-2,3,6-tricarboxyl acid anhydride, 4-(meth)acryloxyethylcarbonyl-propionoyl-1,8-naphthalic acid anhydride or 4-(meth)acryloxy-ethyl-naphthalene-1,3-tricarboxyl acid anhydride.

8. A primer composition according to claim 1, wherein the component (iv) is any one of the initiators and accelerators for polymerization or photopolymerization.

9. A primer composition according to claim 8, wherein the initiators or accelerators are organic peroxides, amines and barbituric acid or derivatives thereof.

10. A primer composition according to claim 9, wherein said initiators or accelerators are benzoyl peroxide, 4,4'-dichlorobenzoyl peroxide, N,N-di(2-hydoxyethyl)-p-toluidine 5-(n-butyl)barbituric acid and/or 1,3,5-trimethylbarbituric acid.

11. A primer composition according to claim 8, wherein the initiators or accelerators for photopolymerization are benzoin, benzoin derivatives, α-diketones and/or amines.

12. A primer composition according to claim 8, wherein said initiators or accelerators are camphorquinone, N,N-di(2-hydroxyethyl)-p-toluidine and/or N,N-dimethylaminoethyl methacrylate.

13. A primer composition according to claim 1, wherein the components (i)–(iv) are divided into arbitrary two or more portions.

14. A primer composition according to claim 1, which additionally comprises a polymerizable compound without hydroxyl group and acidic group.

15. A primer composition according to claim 1, which additionally comprises an organic solvent.

16. A primer composition according to claim 1, which additionally comprises a stabilizer for shelf life.

17. A process for adhering a dental adhesive restorative material to a substrate comprising applying the primer composition according to claim 1, to the substrate and adhering to dental adhesive restorative material to the pretreated substrate directly or through a bonding agent.

18. A process according to claim 17, wherein the dental adhesive restorative materials are dental resin cements, composite resins or polymethyl-methacrylate resins.

19. A process according to claim 17, wherein the substrate is a vital hard tissue.

20. A process according to claim 19, wherein the vital hard tissue is an enamel or a dentin of natural teeth.

21. A process according to claim 17, wherein the substrate is a glass ionomer cement.

* * * * *